US00PP34597P2

(12) United States Plant Patent
Adams

(10) Patent No.: US PP34,597 P2
(45) Date of Patent: Sep. 20, 2022

(54) BLACKBERRY PLANT NAMED 'PS-BK3-17.006-13'

(50) Latin Name: ***Rubus* L. subgenus *Rubus***
Varietal Denomination: PS-BK3-17.006-13

(71) Applicant: PLANT SCIENCES, INC., Watsonville, CA (US)

(72) Inventor: Scott W. Adams, Carmel Valley, CA (US)

(73) Assignee: Plant Sciences, Inc., Watsonville, CA (US)

( * ) Notice: Subject to any disclaimer, the term of this patent is extended or adjusted under 35 U.S.C. 154(b) by 0 days.

(21) Appl. No.: 17/503,081

(22) Filed: Oct. 15, 2021

(51) Int. Cl.
*A01H 5/08* (2018.01)
*A01H 6/74* (2018.01)

(52) U.S. Cl.
USPC ..... Plt./203

(58) Field of Classification Search
USPC ..... Plt./203, 204
CPC ... A01H 5/08; A01H 5/00; A01H 6/74; A01H 6/749; A01H 6/7499
See application file for complete search history.

(56) References Cited

U.S. PATENT DOCUMENTS

PP22,449 P3 * 1/2012 Clark ..... A01H 5/08 Plt./203

OTHER PUBLICATIONS

Trademark Electronic Search System for PRIME-ARK, retrieved on Jan. 20, 2022, retrieved from the Internet at https://tmsearch.uspto.gov/bin/showfield?f=doc&state=4805:2dh1r.3.15, 2 pp. (Year: 2022).*

* cited by examiner

*Primary Examiner* — June Hwu
(74) *Attorney, Agent, or Firm* — Foley & Lardner LLP

(57) ABSTRACT

This invention relates to a new and distinct everbearing variety of blackberry plant named 'PS-BK3-17.006-13'. The new variety is primarily adapted to the growing conditions of the central coast of California and is characterized by the following: mid-season primocane production with medium sized fruit with good flesh and skin firmness. Fruit is of consistent oblong shape, with medium gloss and good flavor. Foliage is slightly convex (u-shaped) and medium green, possessing weak rugosity, weak gloss and 5-foliate leaves. Primocanes have an absent or very weak waxy coat, low thorn density of green thorns and weak anthocyanin coloration.

6 Drawing Sheets

Latin name of the genus and species of the plant claimed: *Rubus* L. subgenus *Rubus*.
Variety denomination: 'PS-BK3-17.006-13'.

BACKGROUND OF THE INVENTION

The present invention relates to a new and distinct fall bearing blackberry plant designated as 'PS-BK3-17.006-13'. This new variety is a result of a controlled cross made in 2017 in Watsonville, Calif. between blackberry variety 'BK3 14.046-34' (unpatented) as the female parent and blackberry variety 'BK3 14.057-02' (unpatented) as the male parent in an ongoing breeding program. The variety is botanically known as *Rubus* L. subgenus *Rubus*.

The seedling resulting from the aforementioned cross was asexually propagated by dormant canes in Santa Cruz County, Calif. and was subsequently selected by the inventor from a controlled breeding plot in Watsonville, Calif. in 2019. After its selection, the new variety was further asexually propagated by dormant canes, roots and non-dormant root shoot cuttings in Santa Cruz County, Calif., San Joaquin County, Calif. and Siskiyou County, Calif. The new variety was then extensively tested over the next several years in fruiting fields in Santa Cruz County, Calif. This propagation has demonstrated that the combination of traits disclosed herein as characterizing the new variety are fixed and remain true to type through successive generations of asexual reproduction.

BRIEF SUMMARY OF THE INVENTION

'PS-BK3-17.006-13' is primarily adapted to the climate and growing conditions of the central coast of California. This region provides the necessary year-round temperatures required for it to produce and maintain a strong vigorous plant and to remain in fruit production from August through December on primocanes and in the ensuing year from June through August on the floricanes. The following traits have been repeatedly observed and are determined to be unique characteristics of 'PS-BK3-17.006-13', which in combination distinguish this blackberry plant as a new and distinct variety:

1. Primocane production
2. Berries with firm flesh and skin
3. Reduced thorn density
4. Fruit with strong adherence to receptacle
5. Good flavor

BRIEF DESCRIPTIONS OF THE DRAWINGS

The accompanying color photographs illustrate the overall appearance of typical specimens of the new blackberry variety, 'PS-BK3-17.006-13' at various stages of development as true as reasonably possible with color reproductions of this type. Color in the photographs may differ slightly from the color value cited in the detailed botanical description which accurately describes the color of 'PS-BK3-17.006-13'. The depicted plant and plant parts of the new blackberry variety 'PS-BK3-17.006-13' were taken in Watsonville, Calif. and are approximately 2 to 16 months old:

DETAILED BOTANICAL DESCRIPTION

Figure 1:
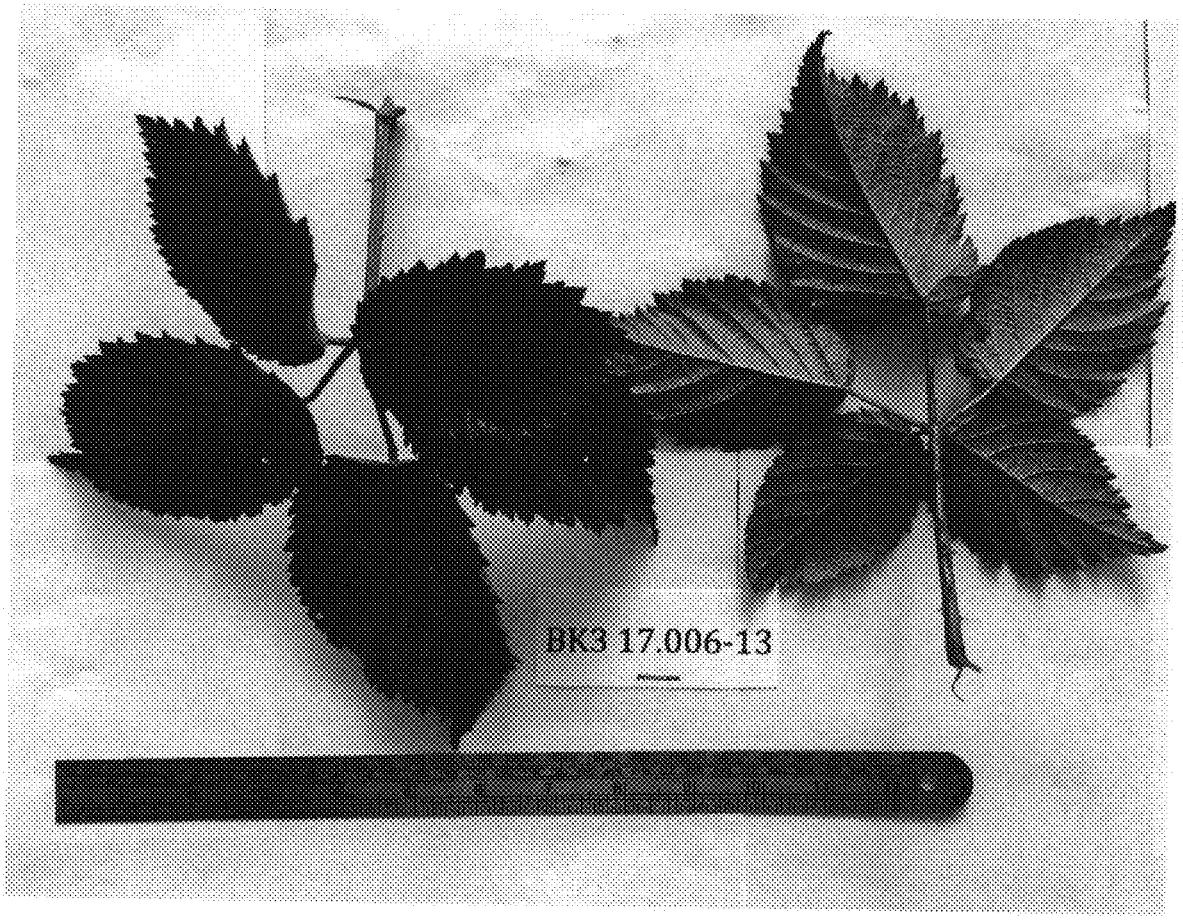
FIG. 1 shows typical floricane leaf color; foliate and rugosity characteristics of 'PS-BK3-17.006-13' taken in the month of March 2020.
Figure 2:
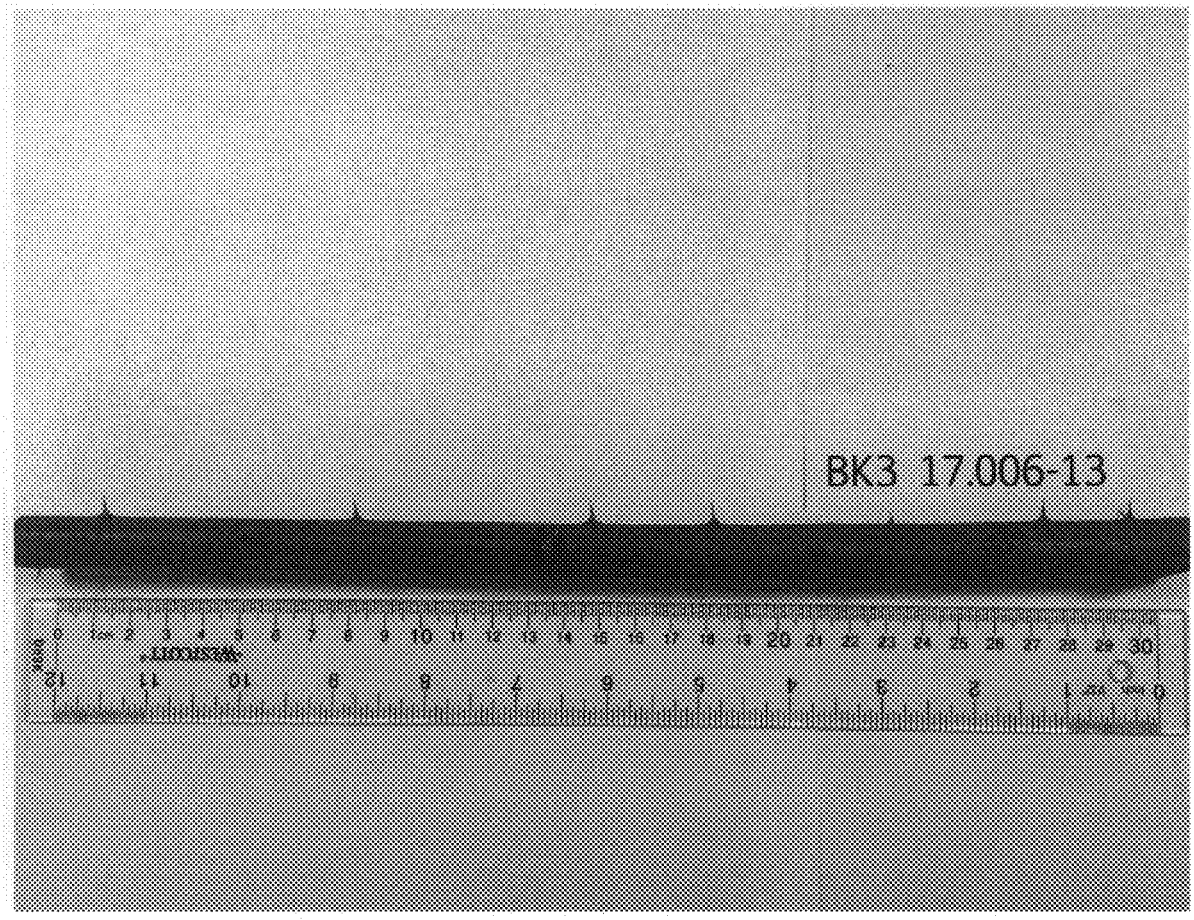
FIG. 2 shows typical primocane coloration, thorn density and coloration of 'PS-BK3-17.006-13' taken in the month of October 2021.
Figure 3:
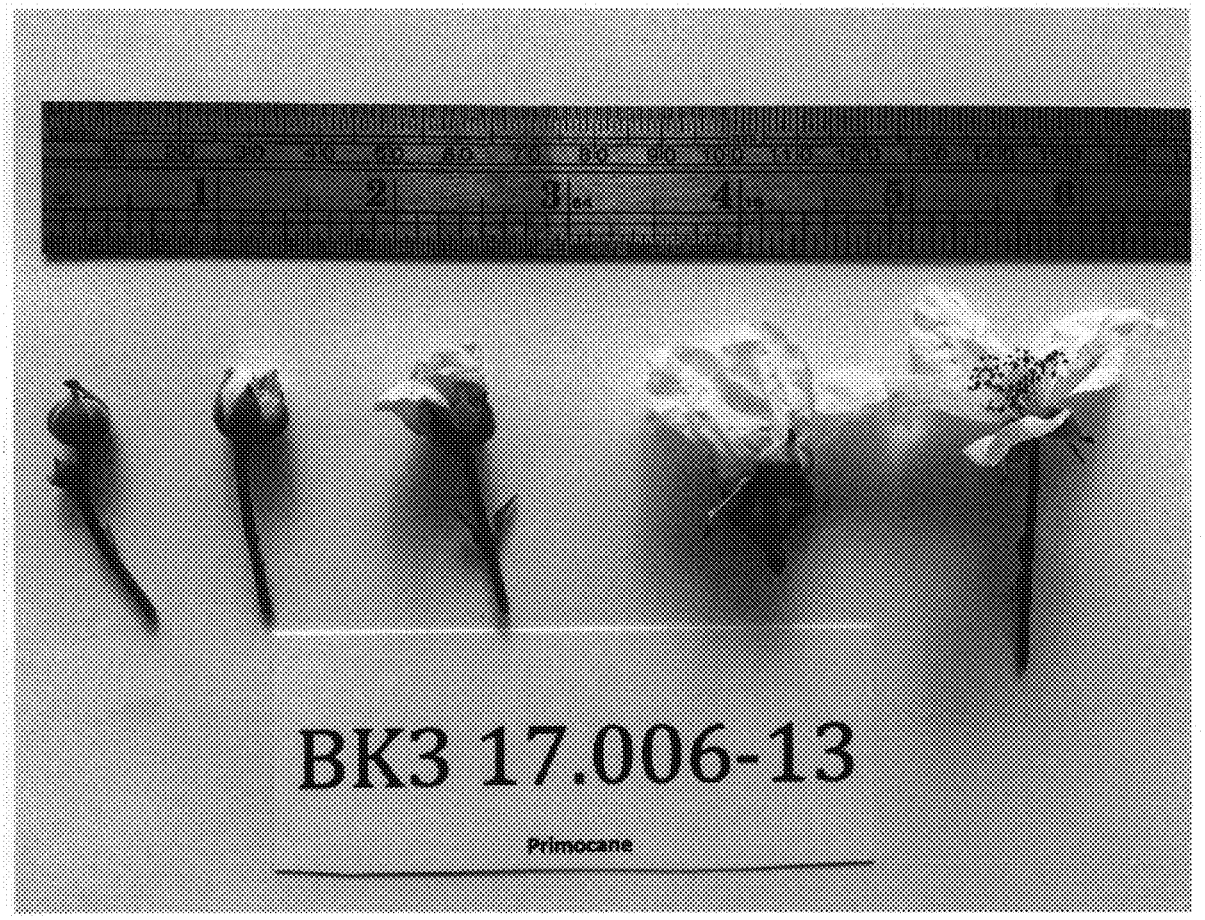
FIG. 3 shows typical primocane flower bud and petal coloration of 'PS-BK3-17.006-13' taken in the month of September 2021.
Figure 4:
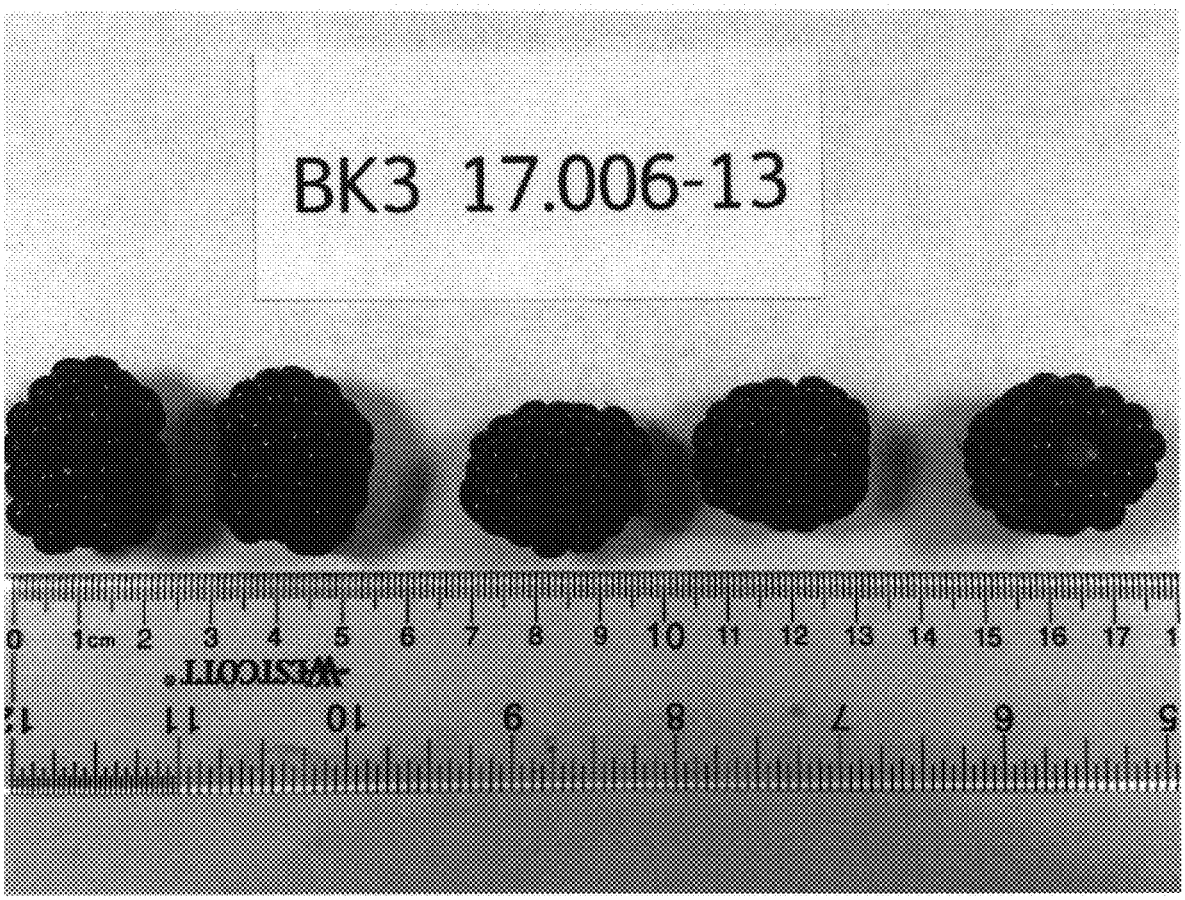
FIG. 4 shows typical primocane fruit and drupelet characteristics of 'PS-BK3-17.006-13' taken in the month of September 2021.
Figure 5:
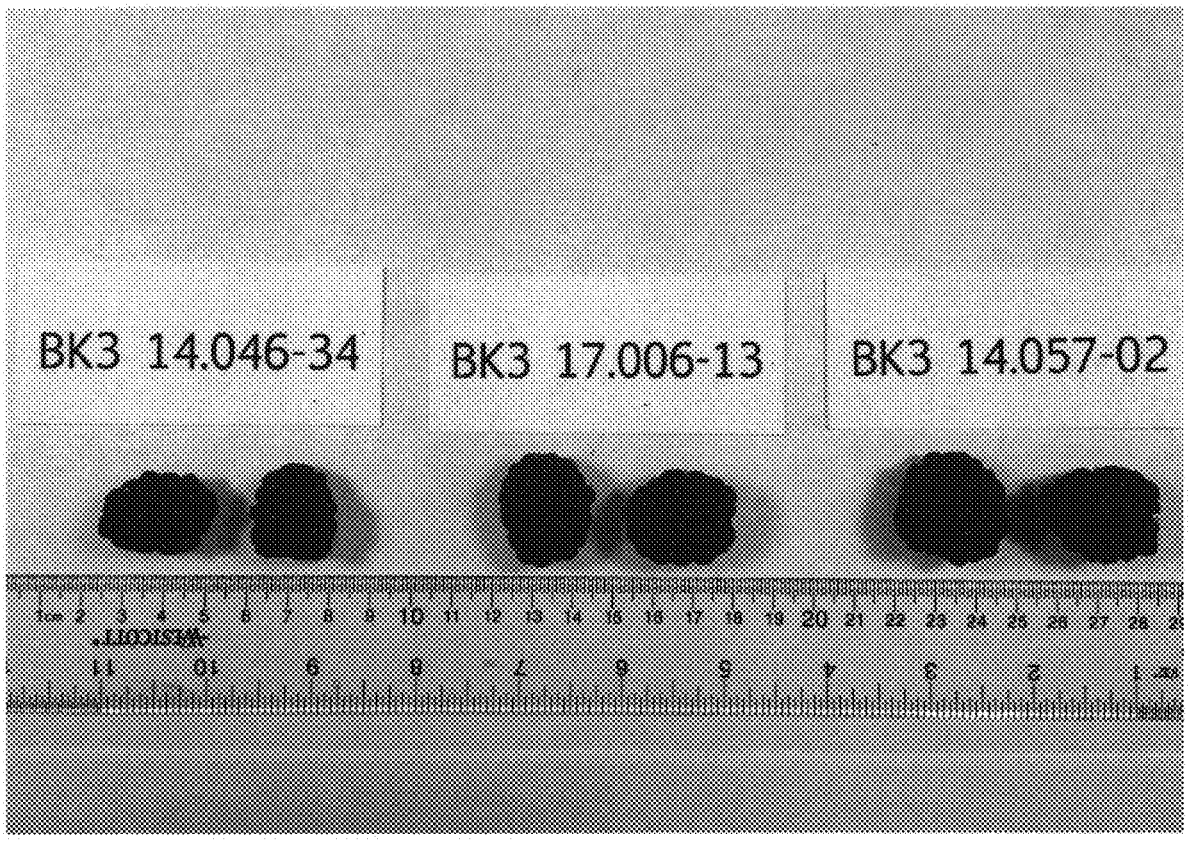
FIG. 5 shows typical floricane fruit characteristics of 'PS-BK3-17.006-13' as compared to those of its parents (female on left; male on right) taken in the month of July 2021.
Figure 6:
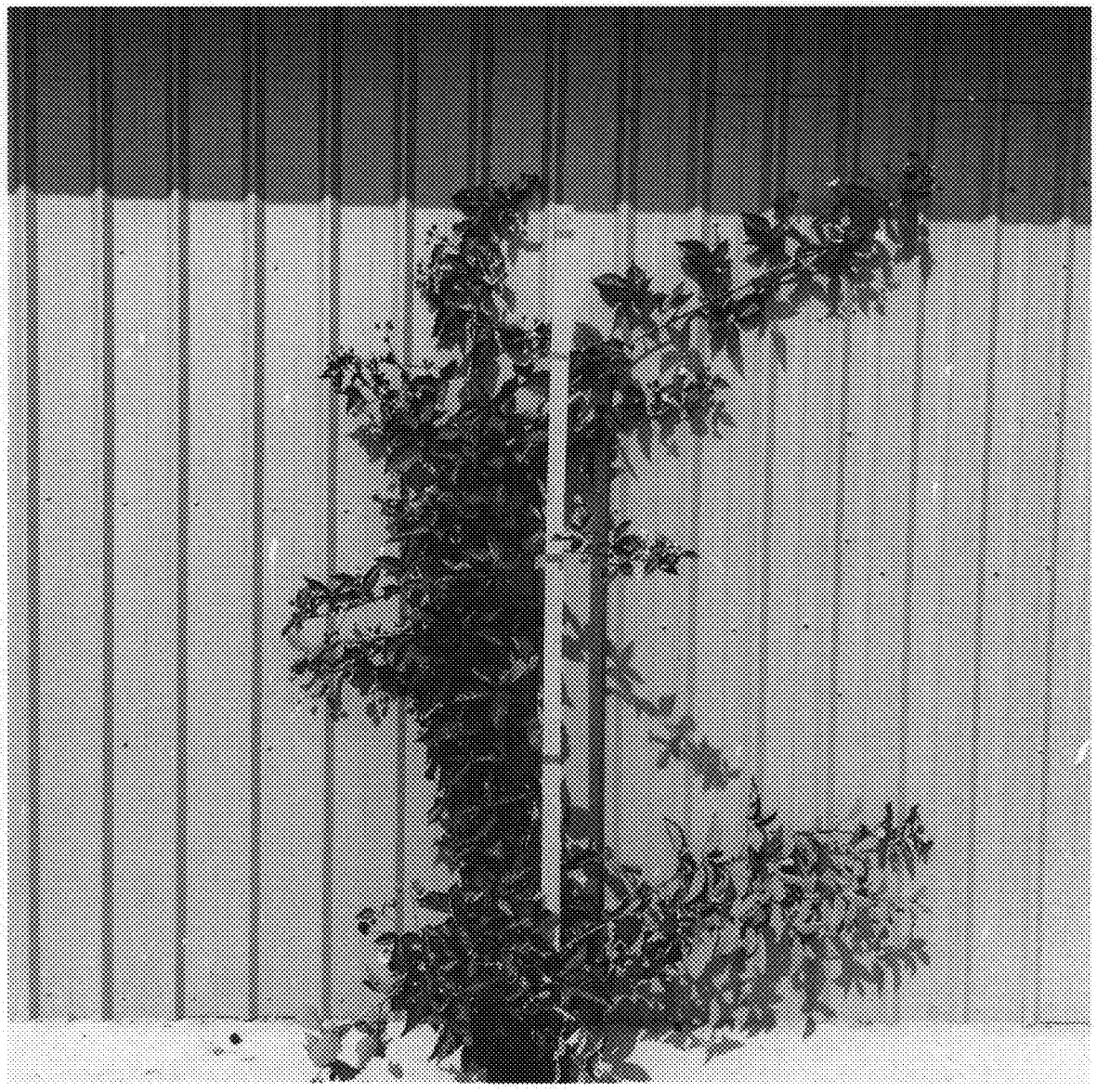
FIG. 6 shows typical primocane plant height and habit of 'PS-BK3-17.006-13' taken in the month of October 2021.

'PS-BK3-17.006-13' has not been observed under all possible environmental conditions. The characteristics of the new variety may vary in detail, depending upon variations in environmental factors, including weather (temperature, humidity and light intensity), day length, soil type, and location.

The aforementioned photographs, together with the following description of the new raspberry variety 'PS-BK3-17.006-13', unless otherwise noted, are based upon observations taken during the 2020-2021 growing season in Watsonville, Calif. Primocane measurements and ratings were taken from plants of 'PS-BK3-17.006-13' produced from a tissue culture lab located in Watsonville, Calif. during the summer of 2020 and planted out mid-December 2020 into trial plots in Watsonville, Calif. The approximate age of the observed primocane plants is 6 to 10 months. Floricane measurements and ratings were taken from the previous year's trial plots of 'PS-BK3-17.006-13' planted in mid-December of 2019 and were observed at an approximate age of 16 to 18 months. Yield observations and fruit quality characteristics are averaged from three years of data collected from the 2019 through 2021 production seasons. Flower measurements and characteristics are from secondary flowers unless otherwise noted. Fruit characteristics and measurements are from secondary fruit unless otherwise noted. Foliage characteristics and measurements are from 5-foliate foliage unless otherwise noted.

Color terminology where noted follows The R.H.S. Colour Chart Sixth Edition (2019 Reprint), Royal Horticultural Society, London, United Kingdom (1966).

The following tables 3-7 describe fruit, plant, foliage, flower and pest/disease characteristics of the new blackberry 'PS-BK3-17.006-13'.

TABLE 3

| FRUIT CHARACTERISTICS | |
|---|---|
| Characteristic | 'PS-BK3-17.006-13' |
| Color mature fruit | RHS 203A<br>Black |
| Fruit length (mm) | 25.86 |

TABLE 3-continued

| FRUIT CHARACTERISTICS | |
|---|---|
| Characteristic | 'PS-BK3-17.006-13' |
| Fruit width (mm) | 22.03 |
| Length/Width ratio | 1.17<br>Longer than broad |
| Fruit predominant shape | Elliptic |
| Drupelets per berry | 73.8 |
| Drupe length (mm) | 4.75 |
| Drupe diameter (mm) | 4.89 |
| Relative size of drupes | Medium |
| Fruit size | Medium |
| Color achenes | RHS 162C<br>Light yellow |
| Seed length (mm) | 3.36 |
| Seed width (mm) | 1.60 |
| Seed weight (mg) | 3.70 |
| Fruit per node | 11.1 |
| Abscission diameter (mm) | 7.36 |
| Abscission color | RHS 157A<br>Pale yellow green |
| Glossiness | Medium |
| Adherence of receptacle | Strong |
| Firmness of flesh | Firm |
| Firmness of skin | Firm |
| Soluble Solids (% brix) | 9.76 |
| Titratable Acidity (% as Citric Acid) | 0.96 |
| Flavor | Good |

TABLE 4

| PLANT CHARACTERISTICS | |
|---|---|
| Characteristic | 'PS-BK3-17.006-13' |
| General: | |
| Habit | Upright to semi-upright |
| Plant height (m) | 2.1 |
| Plant width (cm) | 30 |
| Time to initiate roots (days) | 10-15 |
| Canes per hill | 3.6 |
| Productivity | Medium |
| Self-fruitfulness | Yes |
| Type of bearing | On both previous season and current season canes |
| Primocane: | |
| Color (true) | RHS 144B<br>Strong yellow green |
| Length (cm) | 202.6 |
| Basal diameter (mm) | 20.89 |
| Diameter central ⅓ (mm) | 14.01 |
| Lateral length at central ⅓ (cm) | 38.1 |
| No. fruiting laterals per cane | 13.6 |
| Total nodes per cane | 28 |
| Internode length at central ⅓ (mm) | 64.42 |
| Anthocyanin coloration | RHS 181A<br>Moderate red |
| Anthocyanin intensity | Weak |
| Pubescence | Present |
| Vegetative bud length (mm) | 4.61 |
| Vegetative bud diameter (mm) | 3.82 |
| Vegetative bud shape | Ovate |
| Vegetative bud color | RHS 144B<br>Strong yellow green |
| Strength of waxy coat (glaucosity) | Absent to very weak |
| Time of leaf burst | Medium |
| Time of flowering | Medium |
| Time of fruiting | Medium |
| Length of fruiting season | Long |
| % of total yield | 59% |

TABLE 4-continued

| PLANT CHARACTERISTICS | |
|---|---|
| Characteristic | 'PS-BK3-17.006-13' |
| Flowering period | Late May to Late October |
| Harvest period | Late August to Early December |
| Primocane fruit weight (g) | 7.35 |
| Primocane yield (g/plant) | 3,940 |
| Young Shoots: | |
| Number | 2-3 Few |
| Coloration | RHS 137C Moderate yellow green |
| Intensity of green | Medium |
| Thorns: | |
| Thorn presence | Present |
| Thorn Texture | Rigid |
| Thorn attitude of the tip | Downward |
| Thorn coloration (tip) | RHS 144B Strong yellow green |
| Thorn coloration (base) | RHS 144B Strong yellow green |
| Thorn length at central ⅓ (mm) | 7.04 |
| Thorn width of base at central ⅓ (mm) | 5.35 |
| Thorn density per cm at central ⅓ | 0.81 Few |
| Floricane: | |
| Color (true) | RHS 187B Dark red |
| Length (cm) | 107.22 |
| Width at central ⅓ (mm) | 14.82 |
| Cane shape in cross section | Rounded to angular |
| Total nodes per cane | 14.1 |
| Internode length at central ⅓ (mm) | 68.11 |
| Fruiting lateral attitude | Erect to horizontal |
| Time of bud burst | Medium |
| Time of leaf burst | Medium |
| Time of flowering | Medium |
| Time of fruiting | Medium |
| Length of fruiting season | Medium |
| % of total yield | 41% |
| Flowering period | Late April to Late June |
| Harvest period | Late May to Late July |
| Floricane fruit weight (g) | 6.61 |
| Floricane yield (g/plant) | 2,738 |

TABLE 5

| FOLIAGE CHARACTERISTICS | |
|---|---|
| Characteristic | 'PS-BK3-17.006-13' (5 Foliate) |
| General: | |
| Color of upper surface | RHS NN137A Greyish olive green |
| Color of lower surface | RHS 138A Moderate yellowish green |
| Venation | Pinnate |
| Shape in cross section | Slightly convex |
| Arrangement | Palmate |
| Relief between veins (rugosity) | Weak |
| Glossiness | Weak |
| Margins | Biserrate |
| Number of leaflets/leaf | Five |
| Total leaf length (cm) | 25.6 |
| Total leaf width (cm) | 25.0 |

TABLE 5-continued

| FOLIAGE CHARACTERISTICS | |
|---|---|
| Characteristic | 'PS-BK3-17.006-13' (5 Foliate) |
| Terminal Leaflet: | |
| Length (mm) | 155.11 |
| Width (mm) | 102.96 |
| Length/width ratio | 1.50 Longer than broad |
| Size | Medium |
| Shape | Ovate |
| Shape of tip | Acuminate |
| Shape of base | Cordate |
| Undulation of margin | Weak |
| Shape in cross section | U-shaped |
| Presence of lobing | Absent |
| Margin: depth of incisions | 4.06 |
| Lateral Leaflet (basal pair): | |
| Length (mm) | 99.65 |
| Width (mm) | 59.74 |
| Length/width ratio | 1.7 Much longer than broad |
| Rachis length (mm) | 58.91 |
| Rachis diameter (mm) | 2.44 |
| Rachis anthocyanin coloration of upper surface | RHS 187B Dark red |
| Rachis anthocyanin intensity | Strong |
| Orientation | Opposite |
| Arrangement | Compound |
| Shape | Ovate |
| Relative position of lateral leaflets | Overlapping |
| Shape of the base | Cordate |
| Shape of the tip | Acuminate |
| Petiole: | |
| Length (mm) | 121.05 |
| Diameter (mm) | 4.77 |
| Thorn presence | Present |
| Thorn orientation | Erect |
| Relative number of petiole thorns | 9.1 |
| Anthocyanin coloration of petiole upper surface | RHS 187B Dark red |
| Anthocyanin intensity of petiole upper surface | Medium |
| Color of stipule | RHS 144A Strong yellow green |
| Stipule length (mm) | 15.95 |
| Stipule width (mm) | 1.41 |
| Stipule size | Medium |
| Stipule shape | Subulate |
| Stipule orientation | Erect |
| Stipule arrangement | Free |

TABLE 6

| FLOWER CHARACTERISTICS | |
|---|---|
| Characteristic | 'PS-BK3-17.006-13' |
| Petal color (upper surface) | RHS NN155B Pinkish white |
| Petal color (margin) | RHS 69C Very pale purple |
| Flower diameter (mm) | 44.16 |
| Petal Length (mm) | 21.63 |
| Petal width (mm) | 13.66 |
| Petal length/width ratio | 1.58 Longer than broad |
| Petal shape in cross section | Flat |
| Petal shape (overall) | Obovate |
| Petal shape (apex) | Ovate |
| Petal shape (base) | Obtuse |
| Petal margin | Crenate |

TABLE 6-continued

| FLOWER CHARACTERISTICS | |
|---|---|
| Characteristic | 'PS-BK3-17.006-13' |
| Petal texture | Glabrous |
| No. petals/flower | 5.0 |
| No. sepals/flower | 5.0 |
| Sepal length (mm) | 9.65 |
| Sepal width at base (mm) | 6.40 |
| Sepal shape | Widely deltate |
| Sepal shape (apex) | Acuminate |
| Sepal coloration (upper surface) | RHS 143C<br>Strong yellow green |
| Sepal coloration (lower surface) | RHS 142C<br>Light yellow green |
| Sepal margin | Entire |
| Sepal texture | Pubescent |
| No. stamen/flower | 115 |
| Filament length (mm) | 5.87 |
| Filament color | RHS 155C<br>Greenish white |
| Pollen quantity | High |
| Pollen color | RHS 155B<br>Yellowish white |
| Anther length (mm) | 1.11 |
| Anther diameter (mm) | 0.50 |
| Anther coloration (pre-dehiscence) | RHS 155C<br>Greenish white |
| Anther coloration (post-dehiscence) | RHS 165A<br>Moderate brown |
| Stigma shape | Lobed |
| Stigma length (mm) | 0.11 |
| Stigma diameter (mm) | 0.42 |
| Pedicle length (mm) | 22.89 |
| Pedicle diameter (mm) | 0.98 |
| Pedicle coloration | RHS 144B<br>Strong yellow green |
| Pedicle anthocyanin coloration | RHS 181D<br>Dark yellowish pink |
| Pedicle anthocyanin intensity | Absent to very weak |
| Relative number of pedicel thorns | 1.8<br>Few |
| Peduncle anthocyanin presence | Present |
| Peduncle anthocyanin coloration | RHS 184C<br>Moderate purplish red |
| Peduncle anthocyanin intensity | Absent to very weak |
| Peduncle length (mm) | 88.42 |
| Peduncle diameter (mm) | 3.11 |
| Relative number of peduncle thorns | 4.2 |
| Peduncle thorn length (mm) | 4.67 |
| Peduncle thorn width at base (mm) | 2.39 |

TABLE 7

| PEST AND DISEASE REACTIONS | |
|---|---|
| Characteristic | 'PS-BK3-17.006-13' |
| Spotted wing drosophila (*Drosophila suzukii*) | Susceptible |
| Two spotted spider mite (*Tetranychus urticae*) | Susceptible |
| Red berry mite (*Acahtus essigi*) | Susceptible |
| Grey fruit mold (*Botrytis cinerae*) | Susceptible |
| Powdery mildew (*Podosphaera aphanis* var. *aphanis*) | Moderately resistant |
| Downy mildew (*Peronospora sparsa*) | Susceptible |
| Orange rust (*Arthuriomyces peckianus*) (*Gymnoconia nitens*) | Moderately resistant |

COMPARISON WITH PARENTAL AND COMMERCIAL VARIETIES

'PS-BK3-17.006-13' differs from the proprietary female parent 'BK3 14.046-34' (unpatented) in that 'PS-BK3-17.006-13' has slightly larger, less narrowly oblong fruit shape, smaller drupelet size, a more upright plant habit and later fruit production.

'PS-BK3-17.006-13' differs from the proprietary male parent 'BK3 14.057-02' (unpatented) in that 'PS-BK3-17.006-13' has a less round fruit shape, glossier berries, sweeter flavor and a larger overall primocane yield.

'PS-BK3-17.006-13' differs from the commercial variety 'APF-45' (patented, U.S. Plant Pat. No. 22,449) in that 'PS-BK3-17.006-13' has a smaller, less glossy berry with smaller seeds and sweeter flavor. 'PS-BK3-17.006-13' also has a slightly less upright habit, less overall vigor with both fewer and smaller thorns than 'APF-45'.

For identification, a series of molecular markers have been determined for this new variety.

I claim:

1. A new and distinct variety of blackberry plant named 'PS-BK3-17.006-13', substantially as illustrated and described herein.

* * * * *